US012090341B2

United States Patent
Filiberti et al.

(10) Patent No.: US 12,090,341 B2
(45) Date of Patent: Sep. 17, 2024

(54) POSITION VERIFICATION AND CORRECTION FOR RADIATION THERAPY USING NON-ORTHOGONAL ON-BOARD IMAGING

(71) Applicant: SIEMENS HEALTHINEERS INTERNATIONAL AG, Palo Alto, CA (US)

(72) Inventors: Reto Filiberti, Baar (CH); Niklaus Schär, Wikon (CH)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 353 days.

(21) Appl. No.: 17/549,795

(22) Filed: Dec. 13, 2021

(65) Prior Publication Data
US 2023/0181931 A1 Jun. 15, 2023

(51) Int. Cl.
*A61N 5/10* (2006.01)
*G16H 20/40* (2018.01)

(52) U.S. Cl.
CPC ......... *A61N 5/1049* (2013.01); *A61N 5/1039* (2013.01); *A61N 5/1069* (2013.01);
(Continued)

(58) Field of Classification Search
CPC .. A61N 5/1039; A61N 5/1049; A61N 5/1069; A61N 5/107; A61N 5/1081; A61N 2005/1061; G16H 20/40
See application file for complete search history.

(56) References Cited

U.S. PATENT DOCUMENTS

2014/0046212 A1   2/2014   Deutschmann
2021/0046329 A1   2/2021   Lachaine et al.
(Continued)

FOREIGN PATENT DOCUMENTS

EP   2687159 A1    1/2014
WO   WO-2014108174 A1 *  7/2014   ............. A61B 6/032
(Continued)

OTHER PUBLICATIONS

Chang Zheng et al: "6D image guidance for spinal non-invasive stereotactic body radiation therapy: Comparison between ExacTrac X-ray 6D with kilo-voltage cone-beam CT", Radiotherapy and Oncology, Elsevier, Ireland, vol. 95, No. 1, Apr. 1, 2010 (Apr. 1, 2010), pp. 116-121, XP002696429, ISSN: 0167-8140, DOI:10.1016/J.RADONC.2009.12.036.
(Continued)

*Primary Examiner* — Mark R Gaworecki
(74) *Attorney, Agent, or Firm* — SU IP CONSULTING

(57) ABSTRACT

A computer-implemented method for a radiation therapy system includes: acquiring a first X-ray image of a region while the region is in a first location, the gantry is in a first imaging position, and a center axis of an imaging beam passes through an isocenter of the radiation therapy system along a first imaging path; acquiring a second X-ray image of the region while the region of patient anatomy is in the first location, the gantry is in a second imaging position, and the center axis of the imaging beam passes through the isocenter along a second imaging path, wherein an angle between the first imaging path and the second imaging path is a non-orthogonal angle; and based on the first X-ray image, the second X-ray image, and a three-dimensional treatment planning image of the region, determining an offset between a planning location for the region and the first location.

13 Claims, 9 Drawing Sheets

(52) U.S. Cl.
CPC ............ *A61N 5/107* (2013.01); *A61N 5/1081* (2013.01); *G16H 20/40* (2018.01); *A61N 2005/1061* (2013.01)

(56) References Cited

U.S. PATENT DOCUMENTS

2022/0347490 A1* 11/2022 Novosad .............. A61N 5/1039
2022/0347493 A1* 11/2022 Novosad .............. A61N 5/1049

FOREIGN PATENT DOCUMENTS

| WO | WO-2016128014 A1 * | 8/2016 | ........... A61N 5/1049 |
| WO | WO-2017066248 A1 * | 4/2017 | ............. A61B 6/032 |

OTHER PUBLICATIONS

Willis David J et al: "An Optimized Online Verification Imaging Procedure for External Beam Partial Breast Irradiation" Medical Dosimetry, Elsevier, US, vol. 36, No. 2, Feb. 26, 2010 (Feb. 26, 2010), pp. 171-177, XP028202097, ISSN: 0958-3947, DOI: 10.1016/J.MEDDOS.2010.02.010.

International Search Report and Written Opinion of the International Searching Authority, International Application No. PCT/EP2022/084043, Mar. 27, 2023.

* cited by examiner

POSITION VERIFICATION AND CORRECTION FOR RADIATION THERAPY USING NON-ORTHOGONAL ON-BOARD IMAGING

BACKGROUND

Unless otherwise indicated herein, the approaches described in this section are not prior art to the claims in this application and are not admitted to be prior art by inclusion in this section.

Radiation therapy is a localized treatment for a specific anatomical target, such as a cancerous tumor. Ideally, radiation therapy is performed on the PTV that spares the surrounding normal tissue from receiving doses above specified tolerances, thereby minimizing risk of damage to healthy tissue. Prior to the delivery of radiation therapy, an imaging system is typically employed to provide a three-dimensional image of the anatomical target and surrounding area. From such imaging, the size and mass of the anatomical target can be estimated, a planning target volume (PTV) determined, and an appropriate treatment plan generated using a dedicated treatment planning system.

So that the prescribed radiation dose is supplied accurately to the PTV during radiation therapy, a patient must be correctly positioned relative to the linear accelerator that provides the radiation therapy. Typically, the patient must be precisely positioned so that the PTV is located at the isocenter about which the linear accelerator rotates. Note that depending upon the specific patient and treatment plan, it is possible that the PTV may not be located at the isocenter, however the PTV must still be precisely positioned. To that end, the location of the PTV is pinpointed when treatment planning images are generated, and external patient markings are made that indicate the location of the PTV at the time of treatment. For example, based on the location of the PTV determined via the treatment planning images, a laser-based system can indicate precise locations on the patient for external markings that have a specified relationship to the PTV. Such external patient markings enable the correct positioning of the patient, and therefore the PTV, with respect to a linear accelerator isocenter at the time of treatment.

In most instances, even with the use of external patient markings, accurately positioning a patient precisely at the planned treatment position requires further position verification and correction. Typically, once the patient is positioned on the radiation system couch via a laser-based system, any remaining positional offset of the PTV from the planned treatment position is determined via X-ray imaging or an external surface-monitoring system. Based on such X-ray imaging or surface monitoring, the PTV can then be exactly positioned and oriented to coincide with the planned treatment position, for example by translation and rotation of the radiation system couch.

For certain radiation treatments, such as treatments involving C-arm radiation therapy systems with a couch that can rotate about the system isocenter, on-board imaging included in the radiation therapy system is often unable to provide the X-ray imaging for image-based position verification of an anatomical target. For example, regardless of how far the couch is rotated about the system isocenter, two-dimensional (2D) top-down imaging of an anatomical target can be performed with megavolt imaging, which employs the linear accelerator of the radiation therapy system as an on-board X-ray source. However, such imaging only provides a single 2D view of the anatomical target, and therefore cannot provide positional information along the beam line. Consequently, megavolt imaging cannot provide the detailed position information in three dimensions that is necessary for image-based position verification. Similarly, on-board kilovolt (kV) imaging systems included in a C-arm radiation therapy system cannot be employed for anatomical target position verification in some cases. This is because the couch prevents full rotation of the C-arm gantry for radiation treatments that include rotation of the couch about the system isocenter by more than a few degrees. As a result, there usually is insufficient C-arm gantry rotation to acquire the two orthogonal kV images needed to perform position verification with a 2D-2D match, in which two orthogonal 2D X-ray images of the anatomical target region are aligned with corresponding orthogonal views of a three-dimensional reference image of the anatomical target region.

In light of the above, room-based imaging systems may be employed to perform image-based position verification for C-arm radiation therapy systems. Compared to on-board imaging systems, room-based imaging systems are expensive, involve additional setup, and can require significant space. Further, such systems provide imaging that overlaps in functionality with the on-board X-ray imaging systems already included in C-arm radiation therapy systems.

Accordingly, there is a need in the art for improved techniques to verify patient position for radiation therapy.

SUMMARY

According to various embodiments, a computer-implemented procedure enables position verification and correction for radiation therapy. Specifically, an offset between a planned treatment position for a region of patient anatomy and a current position of the region is determined based on non-orthogonal two-dimensional (2D) X-ray images of the current position of the region, where the 2D X-ray images are acquired with an on-board imaging system. In some embodiments, a first 2D X-ray image is acquired at a first imaging position of a gantry, so that a center axis of an imaging beam passes through an isocenter of the radiation therapy system along a first imaging path, and a second 2D X-ray image is acquired at a second imaging position of the gantry, so that the center axis of the imaging beam passes through the isocenter of the radiation therapy system along a second imaging path that is not orthogonal to the first imaging path. In the embodiments, the offset is determined by a 2D-3D match (also referred to as "2D-3D image registration"). In the 2D-3D match, a three-dimensional (3D) image of the region, such as a treatment planning image, is iteratively repositioned and compared to the first 2D X-ray image and the second 2D X-ray image until the 3D image matches both 2D X-ray images.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
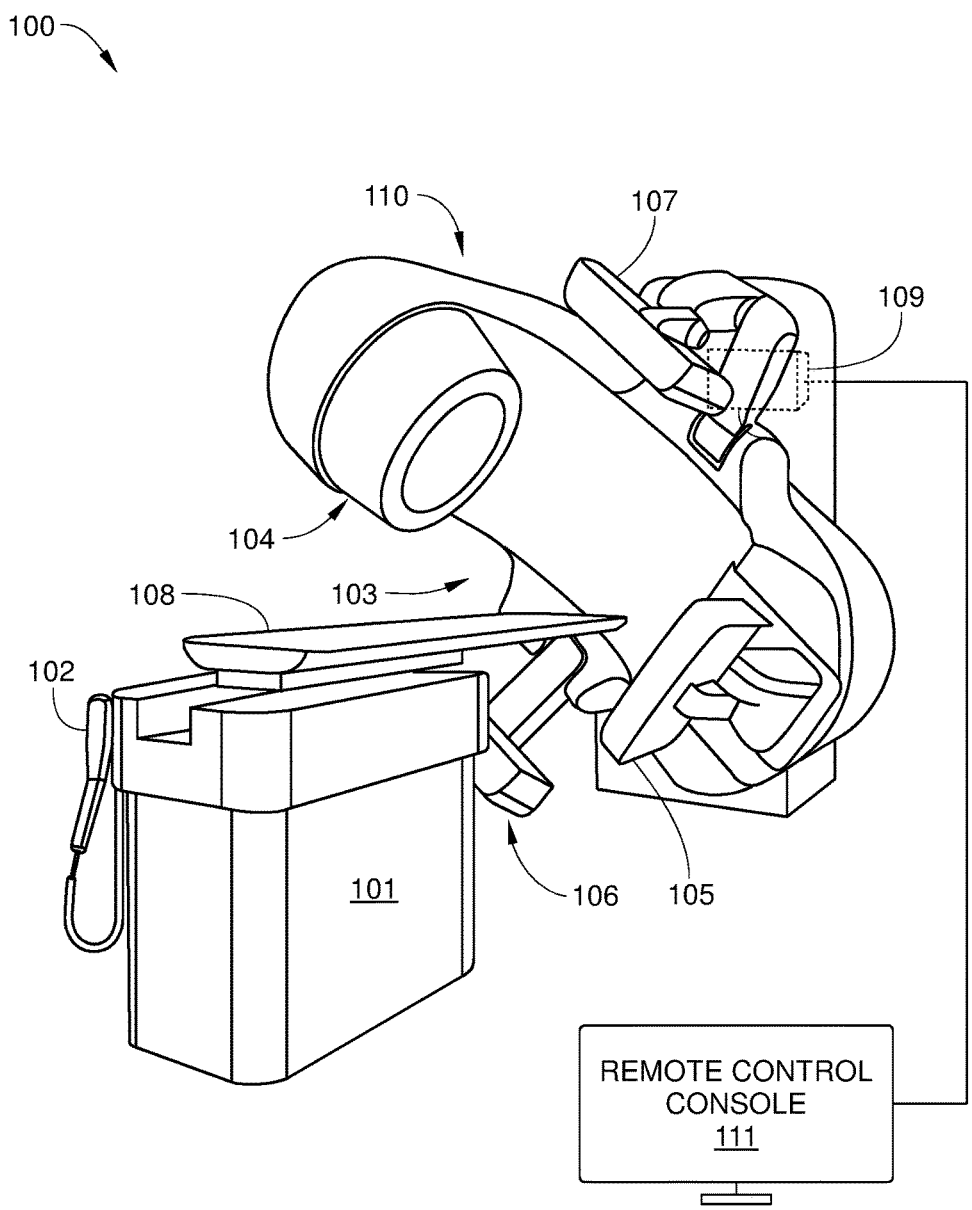
FIG. 1 is a perspective view of a radiation therapy system that can beneficially implement various embodiments.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

System Overview

FIG. 1 is a perspective view of a radiation therapy system 100 that can beneficially implement various embodiments. Radiation therapy (RT) system 100 is a radiation system may be configured to detect intra-fraction motion in near-real time using X-ray imaging techniques. Thus, in some embodiments, RT system 100 is configured to provide stereotactic radiosurgery and precision radiotherapy for lesions, tumors, and conditions anywhere in the body where radiation treatment is indicated. As such, RT system 100 can include one or more of a linear accelerator (LINAC) 104 that generates an MV treatment beam of high energy X-rays or other radiation, one or more kilovolt (kV) X-ray sources 106, one or more imaging panels 107 (e.g., an X-ray imager), and an MV electronic portal imaging device (EPID) 105. By way of example, RT system 100 is described herein configured with a C-arm gantry 110 capable of infinite rotation via a slip ring connection. In other embodiments, RT system 100 can be configured with a circular gantry mounted on a drive stand, or any other technically feasible configuration that enables radiation therapy and imaging of a PTV.

In some embodiments, RT system 100 is capable of X-ray imaging of a target volume immediately prior to and/or during application of an MV treatment beam, so that an image-guided radiation therapy (IGRT) and/or an intensity-modulated radiation therapy (IMRT) process can be performed using X-ray imaging. For example, in some embodiments, RT system 100 includes kV imaging of a PTV in conjunction with imaging generated by the MV treatment beam. RT system 100 may include one or more touchscreens (not shown) for patient information verification, couch motion controls 102, a radiation area 103, a couch positioning assembly 101, a couch 108 disposed on couch positioning assembly 101, and an image acquisition and treatment control computer 109, all of which are disposed within a treatment room. RT system 100 further includes a remote control console 111, which is disposed outside the treatment room and enables treatment delivery and patient monitoring from a remote location. Couch positioning assembly 101 is configured to precisely position couch 108 with respect to radiation area 103. Motion controls 102 include input devices, such as buttons and/or switches, that enable a user to operate couch positioning assembly 101 to automatically and precisely position couch 108 to a predetermined location with respect to radiation area 103. Motion controls 102 also enable a user to manually position couch 108 to a particular location, such as a planned treatment position for a patient or anatomical target.

Figure 2:
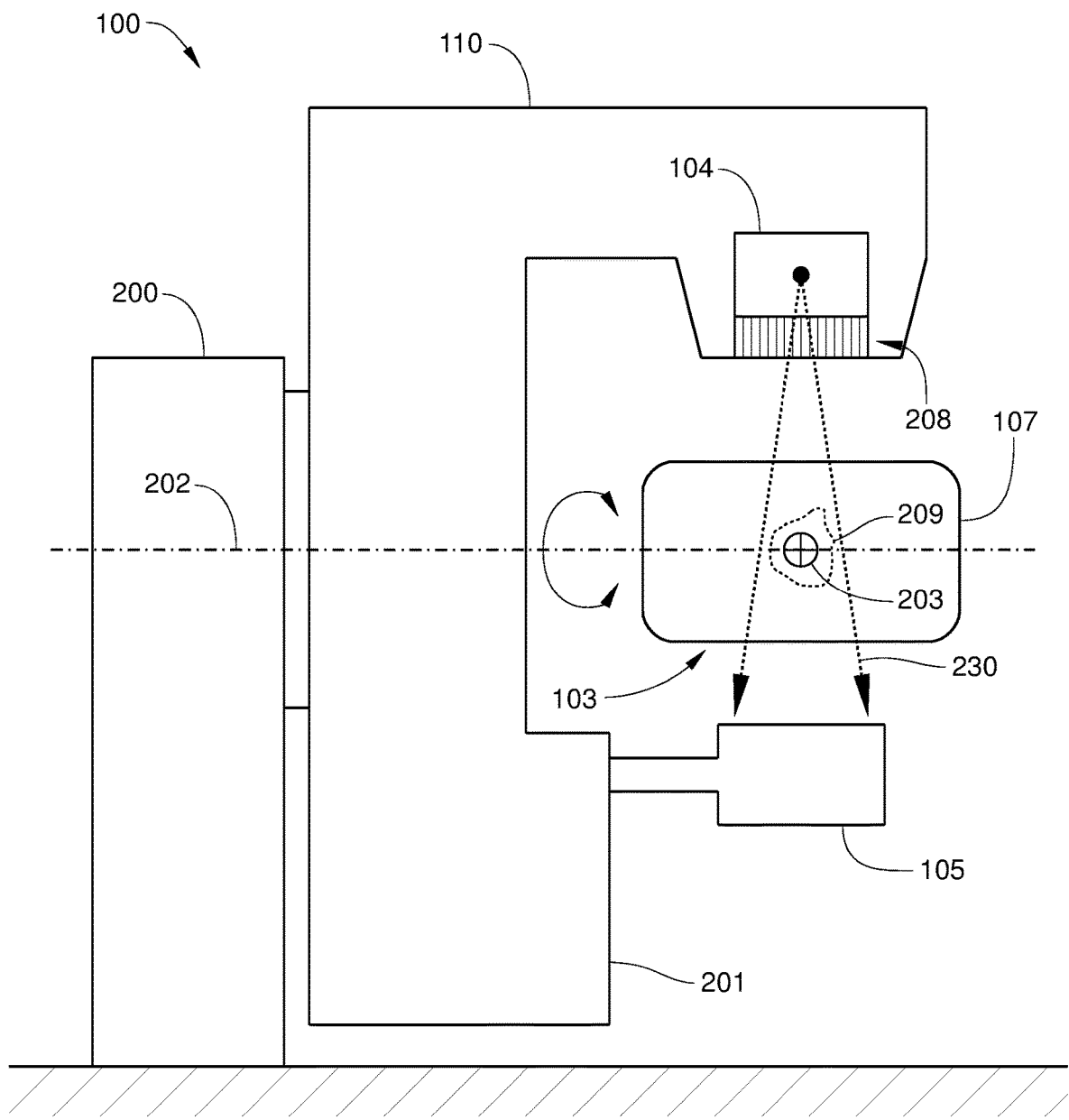
FIG. 2 schematically illustrates a side view of the radiation therapy system of FIG. 1, according to various embodiments.

FIG. 2 schematically illustrates a side view of RT system 100, according to various embodiments. As shown, RT system 100 includes a base stand 200 and C-arm gantry 110. In FIG. 2, couch positioning assembly 101, couch 108, and X-ray source 106 are omitted for clarity. Base stand 200 is a fixed support structure for components of RT treatment system 100, including C-arm gantry 110 and a drive system (not shown) for rotatably moving C-arm gantry 110 about a horizontal rotation axis 202. Base stand 200 rests on and/or is fixed to a support surface that is external to RT treatment system 100, such as a floor of an RT treatment facility. C-arm gantry 110 is rotationally coupled to base stand 200 and is a support structure on which various components of RT system 100 are mounted, including LINAC 104, EPID 105, imaging X-ray source 106 (not shown in FIG. 2), and imaging panel 107. During operation of RT treatment system 100, C-arm gantry 110 rotates about radiation area 103 when actuated by the drive system.

Imaging X-ray source 106 is configured to direct a conical beam of X-rays, referred to herein as imaging X-rays (not shown in FIG. 2 for clarity), through an isocenter 203 of RT system 100 to imaging panel 107. Ideally, isocenter 203 corresponds to the location of a target volume 209 to be treated, such as a PTV, a gross tumor volume (GTV), a clinical target volume (CTV), and/or an internal target volume (ITV), among others. The GTV depicts the position and extent of the gross tumor, for example portions of the tumor that can be seen or imaged; the CTV includes the GTV and an additional margin for sub-clinical disease spread, which is generally not imagable; and the PTV is a geometric concept designed to ensure that a suitable radiotherapy dose is actually delivered to the CTV without adversely affecting nearby organs at risk. Thus, the PTV is generally larger than the CTV, but in some situations can also be reduced in some portions to provide a safety margin around an organ at risk. The PTV is typically determined based on imaging performed prior to the time of treatment, and alignment of the PTV with the current position of patient anatomy at the time of treatment is facilitated by X-ray imaging of a specified region of patient anatomy as described below.

In the embodiment illustrated in FIG. 2, imaging panel 107 is depicted as a planar device, whereas in other embodiments, imaging panel 107 can have a curved configuration. In the embodiment illustrated in FIGS. 1 and 2, RT system 100 includes a single imaging panel and a single corresponding imaging radiation source in addition to EPID 105. In other embodiments, RT system 100 can include two or more imaging panels, each with a corresponding imaging radiation source. Further, in some embodiments, couch positioning assembly 101 is configured to rotate couch 108 sequentially about isocenter 203 to one or more treatment positions. One such embodiment is described below in conjunction with FIG. 3.

Figure 3:
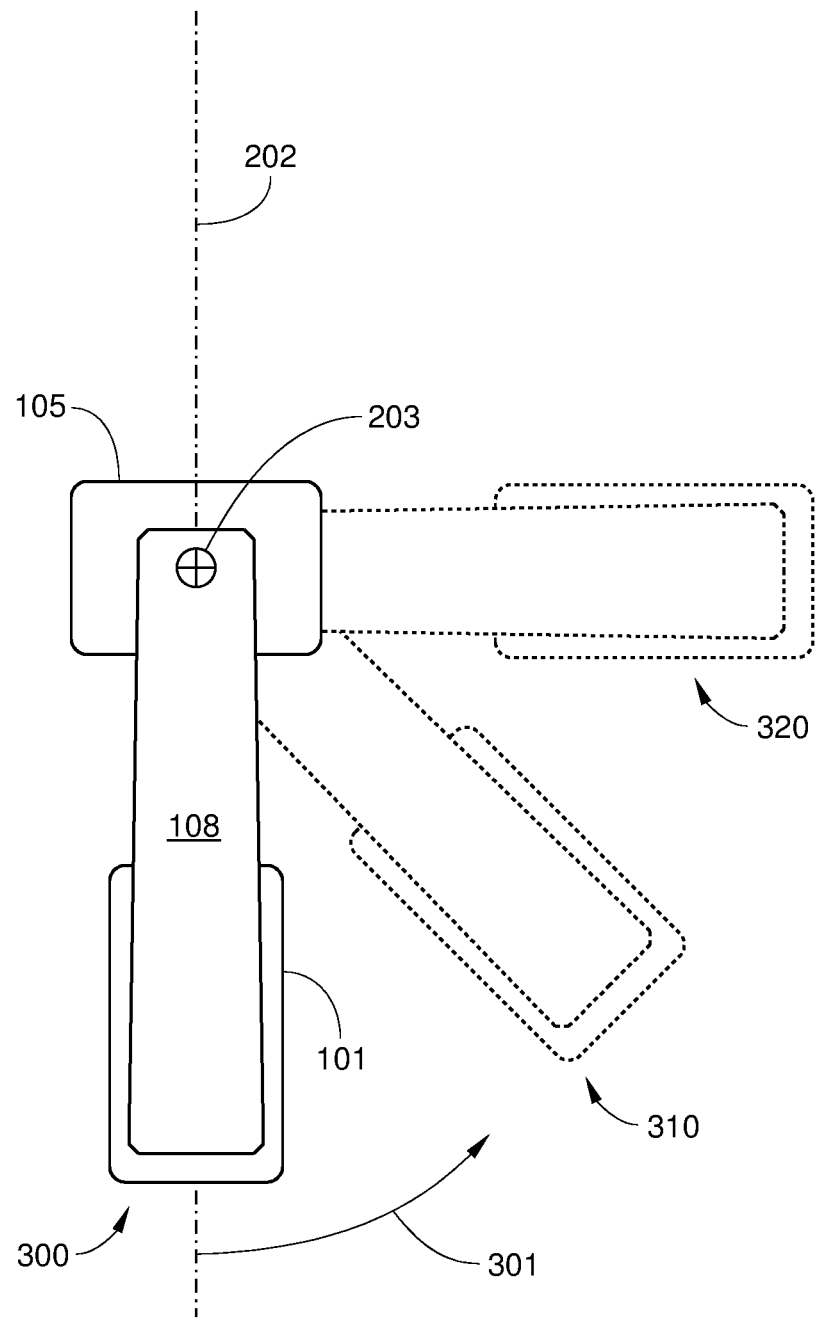
FIG. 3 schematically illustrates plan views of a couch of the radiation therapy system of FIG. 1 in various treatment positions, according to various embodiments.

FIG. 3 schematically illustrates plan views of couch 108 in various treatment positions, according to various embodiments. FIG. 3 includes a plan view of couch 108 in a neutral position 300, in which couch 108 is in line with horizontal rotation axis 202 of C-arm gantry 110, a first rotated position 310 (dashed lines), in which couch 108 is rotated 45 degrees from neutral position 300, and a second rotated position 320 (dashed lines), in which couch 108 is rotated 90 degrees from neutral position 300. For reference, EPID 105 and isocenter 203 are both included in FIG. 3. As shown, couch positioning assembly 101 rotates couch 108 about isocenter 203 to a couch rotational angle 301 from neutral position 300. Couch rotational angle 301 can be, for example, up to about 90 degrees.

Returning to FIG. 2, LINAC 104 typically includes one or more of an electron gun for generating electrons, an accelerating waveguide, an electron beam target, an electron beam transport means (such as a bending magnet) for directing the electron beam to the electron beam target, and/or a collimator assembly 208 for collimating and shaping a treatment beam 230 that originates from the electron beam target. Collimator assembly 208 typically includes one or more of a primary collimator that defines the largest available circular radiation field for treatment beam 230, a secondary collimator for providing a rectangular or square radiation field at isocenter 203 (for example via X-jaws and Y-jaws), and a multileaf collimator (MLC) for conforming treatment beam 230 to a PTV or other anatomical target.

During radiation treatment, in some embodiments LINAC 104 is configured to generate treatment beam 230, which can include high-energy radiation (for example MV X-rays or MV electrons). In other embodiments, treatment beam 230 includes electrons, protons, and/or other heavy charged particles, ultra-high dose rate X-rays (e.g., for FLASH radiotherapy), and/or microbeams for microbeam radiation therapy. In addition, imaging panel 107 is configured to receive imaging radiation and generate suitable projection images therefrom. Further, in some embodiments, as treatment beam 230 is directed to isocenter 203 while C-arm gantry 110 rotates through a treatment arc, image acquisitions can be performed via EPID 105 to generate image data for target volume 209. For example, in such embodiments, EPID 105 generates one or more projection images of target volume 209 and/or a region of patient anatomy surrounding target volume 209. Thus, projection images (e.g., 2D X-ray images) of target volume 209 can be generated during portions of an IGRT or IMRT process via imaging panel 107 and/or EPID 105. Such projection images can then be employed to construct or update portions of imaging data for a digital volume that corresponds to a three-dimensional (3D) region that includes target volume 209. That is, a 3D image of such a 3D region is reconstructed from the projection images. In some embodiments, cone-beam computed tomography (CBCT) and/or digital tomosynthesis (DTS) can be used to process the projection images generated by imaging panel 107.

As noted above, LINAC 104 is configured to generate treatment beam 230 during radiation treatment. For radiation treatments that involve a high radiation dose and/or a small target size, such as stereotactic radiosurgery (SRS) and stereotactic radiotherapy (SRT), the required geometric accuracy of the delivery of treatment beam 230 can be adversely affected by rotation of couch 108 (shown in FIG. 1) about isocenter 203 to various treatment positions. For example, the rotation of couch 108 can cause the patient to shift position on couch 108 or, during the time that couch 108 is rotating to a new rotated position, the patient can move within the mask or other immobilization devices. According to various embodiments, 2D non-orthogonal X-ray images are acquired after couch 108 is rotated to a new rotated position and before treatment is performed at the new rotated position, and the 2D non-orthogonal X-ray images are then employed in a position verification process. In some embodiments, in the position verification process, an offset between a planned treatment position for target volume 209 and a current position of target volume 209 is determined based on non-orthogonal 2D X-ray images via a 2D-3D match process. In some embodiments, a first 2D X-ray image is acquired at a first imaging position and a second 2D X-ray image is acquired at a second imaging position, as described below in conjunction with FIGS. 4-6.

Figure 4:
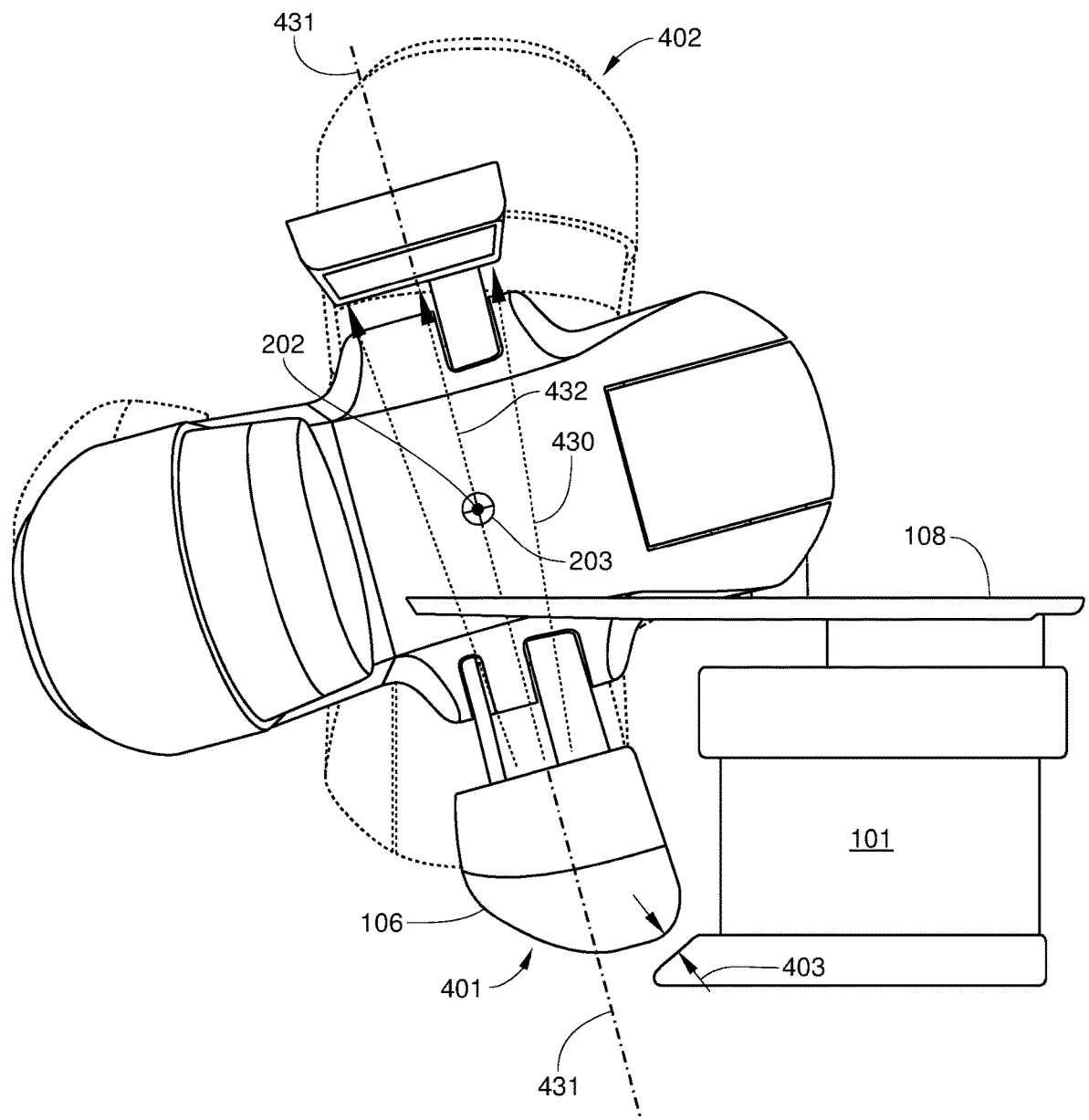
FIG. 4 schematically illustrates a front view of a C-arm gantry of the radiation therapy system of FIG. 1, according to various embodiments.

FIG. 4 schematically illustrates a front view of C-arm gantry 110 of RT system 100, according to various embodiments. Also shown is couch 108, which is rotated to a 90-degree rotated position. In the embodiment illustrated in FIG. 4, C-arm gantry 110 is rotated to a first imaging position 401 relative to a neutral position 402 (dashed lines), so that a center axis 431 of an imaging beam 430 passes from X-ray source 106, through isocenter 203, to imaging panel 107 along a first imaging path 432. Because couch 108 is rotated to a rotated position relative to isocenter 203 in FIG. 4, C-arm gantry 110 cannot rotate freely about horizontal rotation axis 202 without colliding with couch 108. Thus, in first imaging position 401, C-gantry 110 is rotationally displaced counterclockwise from neutral position 402 until a collision is imminent between X-ray source 106 and couch 108 and/or couch positioning assembly 101. For example, in the embodiment illustrated in FIG. 4, C-gantry 110 is rotationally displaced counterclockwise from neutral position 402 until X-ray source 106 is within a clearance distance 403 of couch positioning assembly 101.

Figure 5:
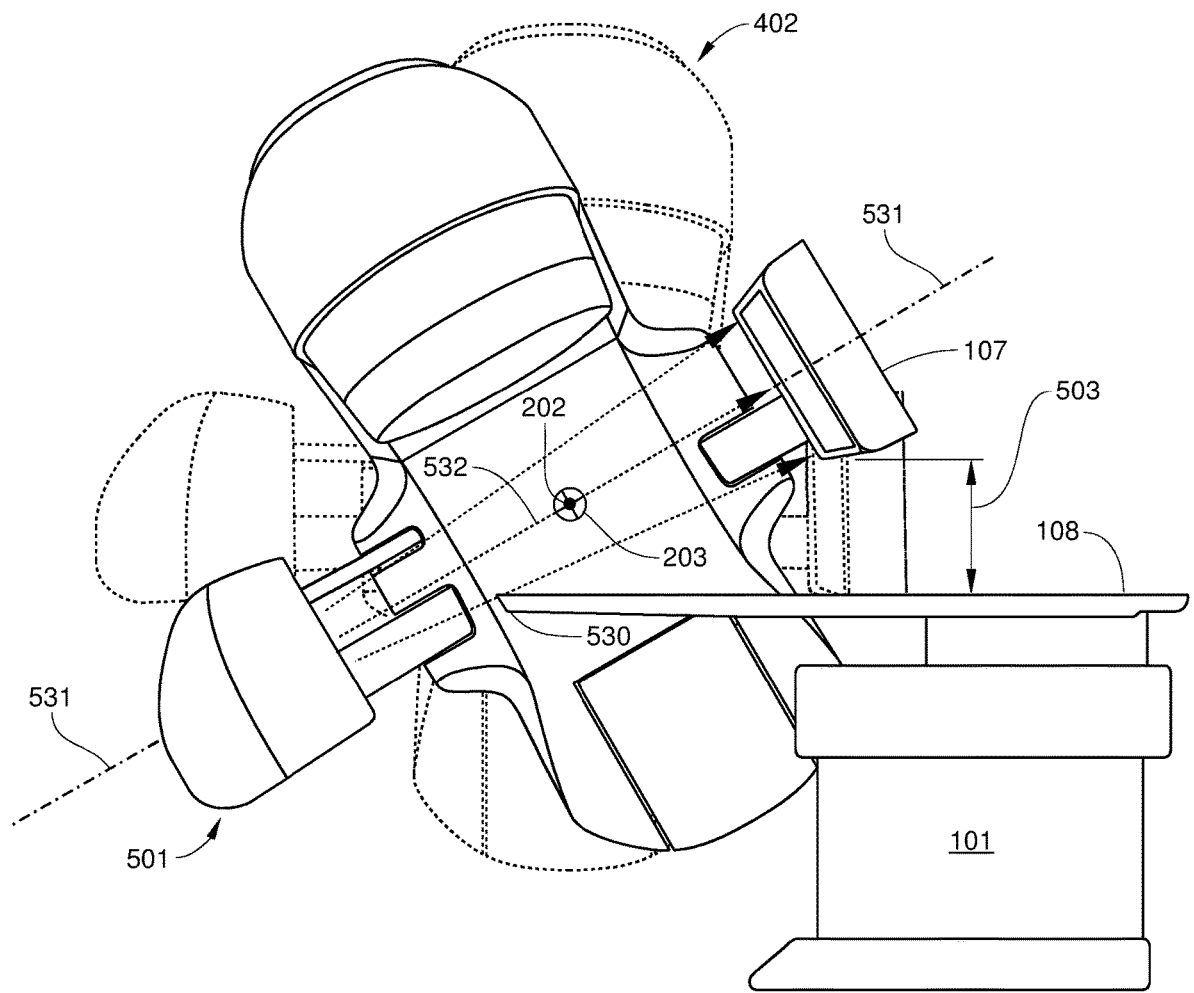
FIG. 5 schematically illustrates a front view of the C-arm gantry of the radiation therapy system of FIG. 1, according to various embodiments.

FIG. 5 schematically illustrates a front view of C-arm gantry 110 of RT system 100, according to various embodiments. Also shown is couch 108, which is rotated to a 90-degree rotated position. In the embodiment illustrated in FIG. 5, C-arm gantry 110 is rotated to a second imaging position 501 relative to neutral position 402 (dashed lines), so that a center axis 531 of an imaging beam 530 passes from X-ray source 106, through isocenter 203, to imaging panel 107 along a second imaging path 532. Because couch 108 is rotated to a rotated position relative to isocenter 203 in FIG. 4, C-arm gantry 110 cannot rotate freely about horizontal rotation axis 202 without colliding with a patient disposed on couch 108. Thus, in second imaging position 501, C-gantry 110 is rotationally displaced clockwise from first imaging position 401 until a collision is possible between imaging panel 107 and a patient disposed on couch 108. For example, in the embodiment illustrated in FIG. 5, C-gantry 110 is rotationally displaced counterclockwise from first imaging position 401 until imaging panel 107 is within a clearance distance 503 of couch 108 or within a clearance distance of a patient disposed on couch 108.

Figure 6:
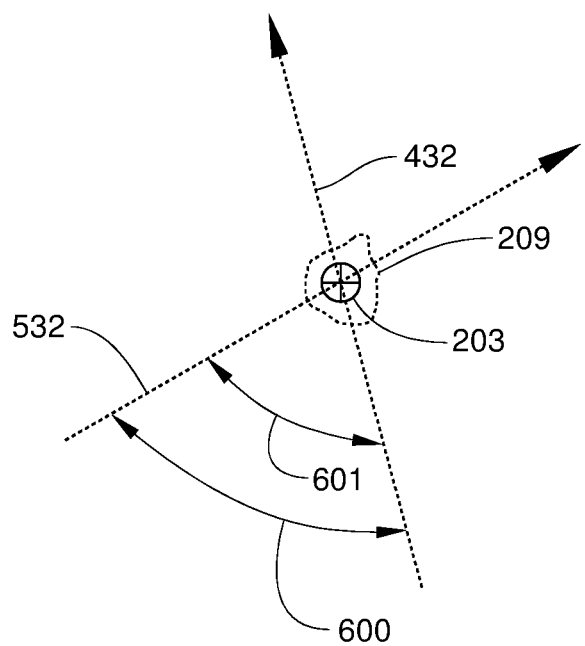
FIG. 6 schematically illustrates a non-orthogonal angle between a first imaging path associated with a first imaging position and a second imaging path associated with a second imaging position, according to various embodiments.

FIG. 6 schematically illustrates a non-orthogonal angle 600 between first imaging path 432 associated with first imaging position 401 (shown in FIG. 4) and second imaging path 532 associated with second imaging position 501 (shown in FIG. 5), according to various embodiments. Due to interference with couch 108 and/or couch positioning assembly 101, non-orthogonal angle 600, which corresponds to the rotational angle between first imaging position 401 and second imaging position 501, is generally less than 90 degrees. In some embodiments, non-orthogonal angle 600 is greater than at least about 30 degrees, so that sufficient spatial information regarding the position of target volume 209 can be captured via X-ray images acquired at first imaging position 401 and second imaging position 501.

In some embodiments, an imaging arc 601 is disposed between first imaging path 432 and second imaging path 532. In such embodiments, additional X-ray images are acquired as imaging panel 107 is rotated through imaging arc 601. In such embodiments, CBCT and/or DTS can be used to process the X-ray projection images generated by imaging panel 107 while imaging panel 107 is rotated through imaging arc 601.

Position Verification and Correction Using on-Board Imaging

Currently, the field of radiation oncology is moving to treating smaller PTVs, for example via stereotactic radiosurgery and stereotactic radiotherapy. Stereotactic radiosurgery and stereotactic radiation therapy are advanced forms of radiation therapy that involve delivery of a high radiation dose to a small focused region of a patient's anatomy. Because of the high radiation dose and small target volumes associated with these treatments, high geometric accuracy of the delivered treatment is required. According to various embodiments, position verification and correction for stereotactic radiosurgery, stereotactic radiotherapy, and other radiotherapies can be implemented using on-board imaging systems. One such embodiment is described below in conjunction with FIG. 7.

Figure 7:
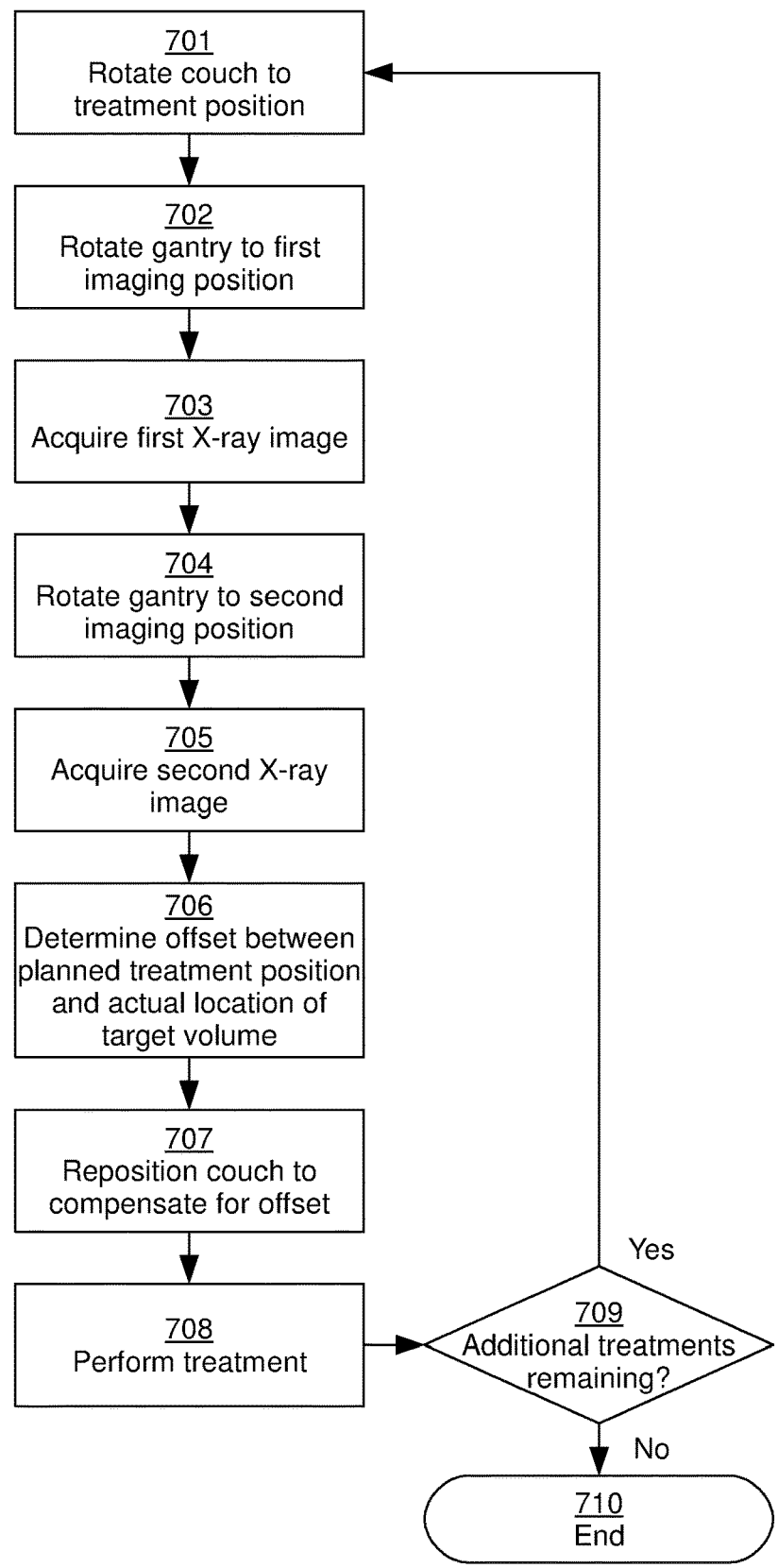
FIG. 7 sets forth a flowchart of a computer-implemented method for a radiation therapy system that includes a gantry and an X-ray imaging system mounted on the gantry, according to one or more embodiments.

FIG. 7 sets forth a flowchart of a computer-implemented method 700 for a radiation therapy system that includes a gantry and an X-ray imaging system mounted on the gantry, according to one or more embodiments. Computer-implemented method 700 can be performed as a part of a radiation therapy process, such as a radiation therapy process that involves rotation of a patient couch about an isocenter of the radiation therapy system for certain portions of the process.

Computer-implemented method 700 may include one or more operations, functions, or actions, as illustrated by one or more of blocks 701-710. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although computer-implemented method 700 is described in conjunction with RT system 100 and FIGS. 1-6, persons skilled in the art will understand that any suitably configured X-ray imaging system is within the scope of the present embodiments.

The control algorithms for the blocks of computer-implemented method 700 may be performed by any suitable computing device or devices. For example, in some embodiments, some or all of the control algorithms for the blocks of computer-implemented method 700 reside in image acquisition and treatment control computer 109, remote control console 111, a combination of both, or any other computing device communicatively coupled to RT system 100. The control algorithms can be implemented in whole or in part as software- or firmware-implemented logic, and/or as hardware-implemented logic circuits.

Prior to computer-implemented method 700, a patient is positioned on couch 108 while couch 108 is in neutral position 300. Then, the position of the patient relative to isocenter 203 and/or a planned treatment position is verified (for example via on-board CBCT imaging of a region of patient anatomy that includes target volume 209), and couch 108 is translated and/or rotated to precisely position target volume 209 at the planned treatment position. Thus, prior to computer-implemented method 700, the location and orientation of target volume 209 is corrected to correspond to the planned treatment position. In some embodiments, radiation treatment is then performed, in which treatment beam 230 is directed to target volume 209, either from one or more gantry angles, or while C-arm gantry 110 rotates through a specified treatment arc.

In step 701, couch 108 is rotated about isocenter 203 to a specified rotated treatment position for the next treatment, either from one or more gantry angles, or an arc treatment. In some embodiments, the specified rotated treatment position may correspond to a rotation of couch 108 about isocenter 203 by as much as +90 degrees or −90 degrees from neutral position 300. For example, various cranial radiotherapy treatments involve positioning a patient at multiple different rotated treatment positions with respect to isocenter 203 and applying treatment beam 230 at each rotated treatment position.

In step 702, C-arm gantry 110 is rotated about isocenter 203 to first imaging position 401. In step 703, while C-arm gantry 110 is at first imaging position 401, a first X-ray image (such as a 2D projection image) is acquired of a region of patient anatomy that includes target volume 209. In some embodiments, the first X-ray image is acquired with X-ray source 106 and imaging panel 107. Additionally or alternatively, in some embodiments, in step 702 an X-ray image is acquired via LINAC 104 and EPID 105. Thus, in such embodiments, multiple X-ray images can be acquired while C-arm gantry 110 is at first imaging position 401.

In step 704, C-arm gantry 110 is rotated about isocenter 203 to second imaging position 501. In some embodiments, no X-ray images are acquired while C-arm gantry 110 rotates about isocenter 203 to second imaging position 501. In other embodiments, multiple X-ray images are acquired while C-arm gantry 110 rotates about isocenter 203 to second imaging position 501 (for example to enable on-board CBCT/DTS imaging of the region of patient anatomy that includes target volume 209). In such embodiments, the CBCT imaging enables generation of a 3D image of the region of patient anatomy that includes target volume 209. This 3D image can be employed in position verification of target volume 209.

In step 705, while C-arm gantry 110 is at second imaging position 501, a second X-ray image (such as a 2D projection image) is acquired of the region of patient anatomy that includes target volume 209. In some embodiments, the second X-ray image is acquired with X-ray source 106 and imaging panel 107. Additionally or alternatively, in some embodiments, in step 705 an X-ray image is acquired via LINAC 104 and EPID 105. Thus, in such embodiments, multiple X-ray images can be acquired while C-arm gantry 110 is at second imaging position 401.

In step 706, RT system 100 determines an offset between the planned treatment position of target volume 209 and the actual location of target volume 209. It is noted that for each rotated position of couch 108, there is generally a different planned treatment position for target volume 209, since the orientation of target volume 209 changes as couch 108 is rotated about isocenter 203.

In some embodiments, a 2D-3D matching algorithm is employed in step 706 to determine the offset. In such embodiments, the 2D-3D matching algorithm is iteratively applied using the first X-ray image, the second X-ray image, and a 3D treatment planning image on which the current radiation therapy is based. Specifically, the 3D treatment planning image is virtually positioned at the planned treatment position of target volume 209 as a "first guess" for the current position of target volume 209. Then, a first virtual X-ray image (such as a digitally reconstructed radiograph or equivalent) is generated based on a view of the 3D treatment planning image along first imaging path 432, and a second virtual X-ray image is generated based on a view of the 3D treatment planning image along second imaging path 532. The first virtual X-ray image is virtually compared to the first X-ray image, and the second virtual X-ray image is virtually compared to the second X-ray image. Based on the comparison, the 2D-3D matching algorithm determines a new virtual location for the 3D treatment planning image that is likely to be closer to the current actual position of target volume 209. The above process repeats until the first virtual X-ray image converges to the first X-ray image and the second virtual X-ray image converges to the second X-ray image. That is, the above process repeats until differences between the first virtual X-ray image and the first X-ray image fall below a specified threshold and differences between the second virtual X-ray image and the second X-ray image fall below a specified threshold.

It is noted that a conventional 2D-3D matching algorithm can generally be employed to perform the above-described process and converge to the current actual position of target volume 209. By contrast, when first X-ray image and second X-ray image are not orthogonal, a human operator generally cannot visually perform an equivalent process. First, the first virtual X-ray image and the second virtual X-ray image are typically not acquired from a frontal, axial or sagittal viewing position, and therefore are difficult for a human operator to interpret. Second, due to the interdependencies of the first virtual X-ray image and the second virtual X-ray image in more than one degree of freedom, virtually repositioning the 3D treatment planning image in any single direction changes both the first virtual X-ray image and the second virtual X-ray image with each iteration. This makes a visual determination of whether the new virtual position of target volume 209 is closer to the actual position of target volume 209 extremely difficult, if not impossible. Thus, given a first X-ray image and a second X-ray image of target volume 209 that are not orthogonal, a human operator can repeatedly reposition the 3D treatment planning image without being able to distinguish whether a new position of the 3D treatment planning image is closer to the actual position of target volume 209.

In some embodiments, a 3D-3D matching algorithm is employed in step 706 to determine the offset. In such embodiments, the 3D-3D matching algorithm can be iteratively applied using a 3D treatment planning image on which the current radiation therapy is based and a 3D volume that is reconstructed based on X-ray images acquired in step 704 (when C-arm gantry 110 is rotated about isocenter 203 from first imaging position 401 to second imaging position 501). In some embodiments, any conventional 3D-3D image registration algorithm can be employed to determine the offset between the 3D treatment planning image and the reconstructed 3D volume.

In step 707, RT system 100 repositions couch 108 based on the offset determined in step 706. In some embodiments, based on the offset determined in step 706, couch 108 is translated and/or rotated to precisely position target volume 209 at the planned treatment position. For example, in some embodiments, RT system repositions couch 108 in up to six degrees of freedom, including translation along a longitudinal axis, a lateral axis, and/or a vertical axis and rotation about a vertical axis (also referred to as a "yaw axis"), rotation about a longitudinal axis (also referred to as a "roll axis"), and/or rotation about a lateral axis (also referred to as a "pitch axis"). Thus, in step 707, RT system 100 compensates for the offset determined between the current actual location of target volume 209 and the planned treatment position of target volume 209, which can include a linear displacement and/or a rotational displacement. In step 708, RT system 100 performs a portion of a radiation therapy treatment associated with the current rotated position of couch 108.

In step 709, RT system 100 determines whether there are any remaining portions of a radiation therapy treatment to be performed at other rotated positions of couch 108. If yes, computer-implemented method 700 returns to step 701; if no, computer-implemented method 700 proceeds to step 710 and terminates.

Implementation of computer-implemented process 700 enables position verification and correction with on-board imaging systems. Thus, embodiments described herein obviate the need for room-based imaging systems and/or external surface-monitoring systems. Further, because acquisition of the first X-ray image and the second X-ray image can be performed quickly, embodiments described herein can be beneficially employed for rapid and accurate position verification for radiotherapy treatments that do not involve rotation of a couch about an isocenter of the radiation therapy system.

Exemplary Computing Device

Figure 8:
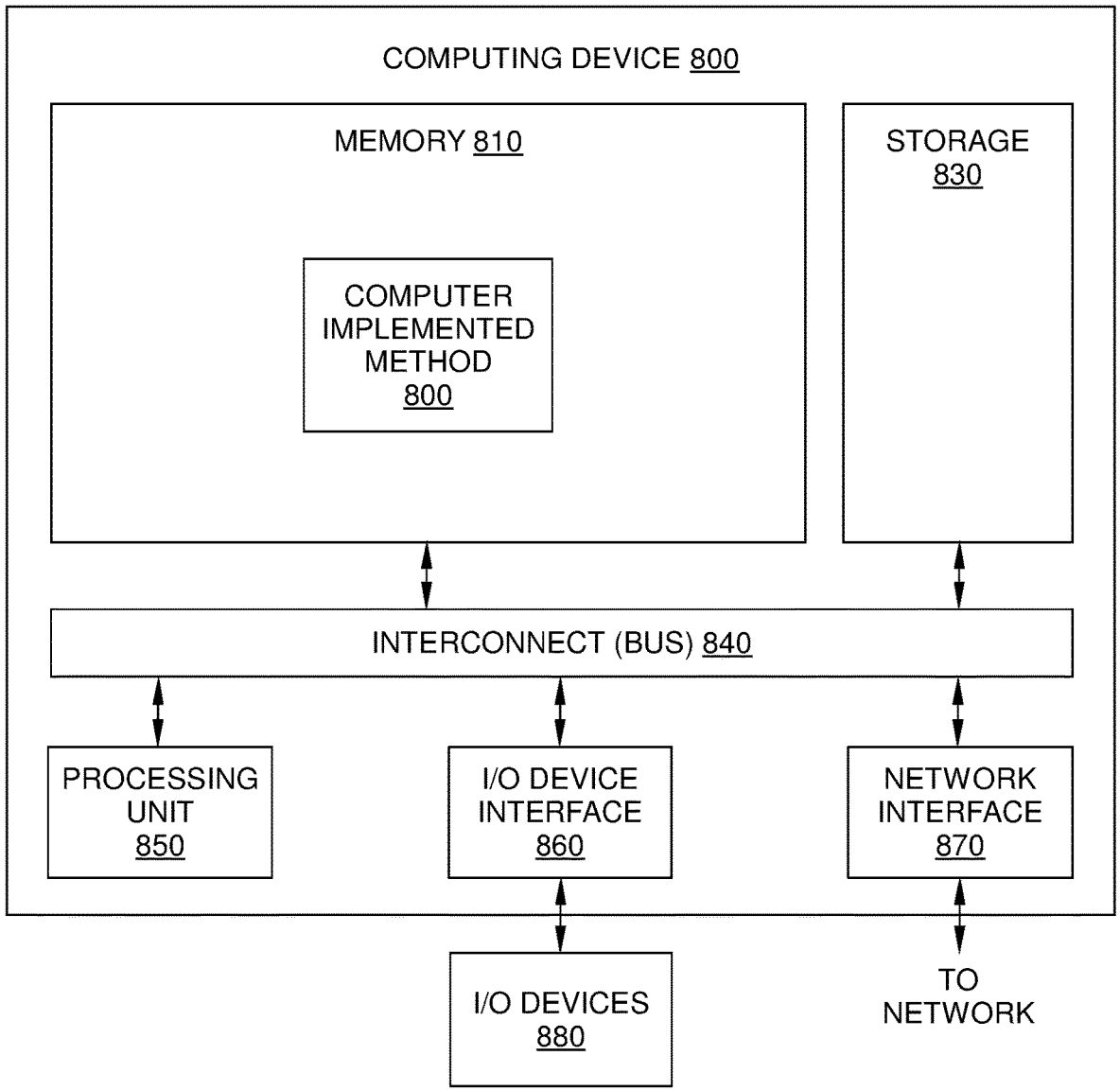
FIG. 8 is an illustration of computing device configured to perform various embodiments.

FIG. 8 is an illustration of a computing device 800 configured to perform various embodiments. Computing device 800 may be a desktop computer, a laptop computer, a smart phone, or any other type of computing device suitable for practicing one or more embodiments of the present disclosure, including image acquisition and treatment control computer 109 and/or remote control console 111. In operation, computing device 800 is configured to execute instructions associated with computer-implemented method 700 as described herein. It is noted that the computing device described herein is illustrative and that any other technically feasible configurations fall within the scope of the present disclosure.

As shown, computing device 800 includes, without limitation, an interconnect (bus) 840 that connects a processing unit 850, an input/output (I/O) device interface 860 coupled to input/output (I/O) devices 880, memory 810, a storage 830, and a network interface 870. Processing unit 850 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 850 may be any technically feasible hardware unit capable of processing data and/or executing software applications, including computer-implemented method 700.

I/O devices 880 may include devices capable of providing input, such as a keyboard, a mouse, a touch-sensitive screen, and so forth, as well as devices capable of providing output, such as a display device and the like. Additionally, I/O devices 880 may include devices capable of both receiving input and providing output, such as a touchscreen, a universal serial bus (USB) port, and so forth. I/O devices 880 may be configured to receive various types of input from an end-user of computing device 800, and to also provide various types of output to the end-user of computing device 800, such as displayed digital images or digital videos. In some embodiments, one or more of I/O devices 880 are configured to couple computing device 800 to a network.

Memory 810 may include a random access memory (RAM) module, a flash memory unit, or any other type of memory unit or combination thereof. Processing unit 850, I/O device interface 860, and network interface 870 are configured to read data from and write data to memory 810. Memory 810 includes various software programs that can be executed by processor 850 and application data associated with said software programs, including computer-implemented method 700.

Exemplary Computer Program Product

Figure 9:
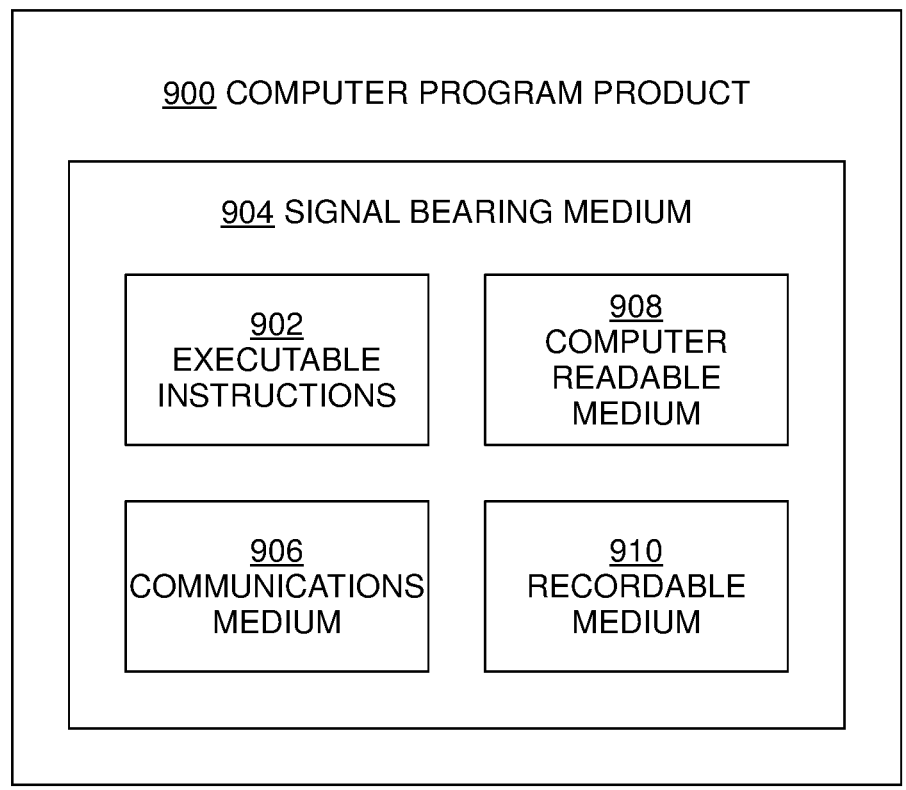
FIG. 9 is a block diagram of an illustrative embodiment of a computer program product for implementing a method for segmenting an image, according to one or more embodiments.

FIG. 9 is a block diagram of an illustrative embodiment of a computer program product 900 for implementing computer-implemented method 700, according to one or more embodiments. Computer program product 900 may include a signal bearing medium 904. Signal bearing medium 904 may include one or more sets of executable instructions 902 that, when executed by, for example, a processor of a computing device, may provide at least the functionality described above with respect to FIGS. 1-8.

In some implementations, signal bearing medium 904 may encompass a non-transitory computer readable medium 908, such as, but not limited to, a solid-state drive, a hard disk drive, a Compact Disc (CD), a Digital Video Disk (DVD), a digital tape, memory, etc. In some implementations, signal bearing medium 904 may encompass a recordable medium 910, such as, but not limited to, memory, read/write (R/W) CDs, R/W DVDs, etc. In some implementations, signal bearing medium 904 may encompass a communications medium 906, such as, but not limited to, a digital and/or an analog communication medium (e.g., a fiber optic cable, a waveguide, a wired communications link, a wireless communication link, etc.). Computer program product 900 may be recorded on non-transitory computer readable medium 908 or another similar recordable medium 910.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A computer-implemented method for a radiation therapy system that includes a gantry and an X-ray imaging system mounted on the gantry, the method comprising:
    acquiring a first X-ray image of a region of patient anatomy while the region of patient anatomy is in a first location relative to an isocenter of the radiation therapy system, the gantry is in a first imaging position, and a center axis of an imaging beam passes through the isocenter of the radiation therapy system along a first imaging path;
    acquiring a second X-ray image of the region of patient anatomy while the region of patient anatomy is in the first location, the gantry is in a second imaging position, and the center axis of the imaging beam passes through the isocenter of the radiation therapy system along a second imaging path, wherein an angle between the first imaging path and the second imaging path is a non-orthogonal angle; and
    based on the first X-ray image, the second X-ray image, and a three-dimensional treatment planning image of the region, determining an offset between a planning location for the region and the first location of the region,
    wherein determining the offset between the planned treatment position for the region and the first location of the region comprises iteratively applying a two-dimensional to three-dimensional matching algorithm to the first X-ray image, the second X-ray image, and the three-dimensional treatment planning image.

2. The computer-implemented method of claim 1, further comprising, causing a movable couch of the radiation therapy system to reposition the region of patient anatomy based on the offset.

3. The computer-implemented method of claim 2, further comprising, in response to the movable couch repositioning the region, causing a treatment beam to be directed to the region.

4. The computer-implemented method of claim 2, wherein causing the movable couch to reposition the region comprises causing the movable couch to rotate or translate the region.

5. The computer-implemented method of claim 1, wherein the offset includes at least one of a linear displacement and a rotational displacement.

6. The computer-implemented method of claim 1, further comprising:
- after acquiring the first X-ray image of the region, causing the gantry to rotate from the first imaging position to the second imaging position;
- acquiring one or more additional X-ray images while the gantry rotates from the first imaging position to the second imaging position; and
- generating a reconstructed three-dimensional image of the region based on the first X-ray image, the second X-ray image, and the additional X-ray images.

7. The computer-implemented method of claim 6, wherein determining the offset between the planned treatment position for the region and the first location of the region comprises iteratively applying a three-dimensional to three-dimensional matching algorithm to the reconstructed three-dimensional image of the region and the three-dimensional treatment planning image.

8. The computer-implemented method of claim 1, wherein the three-dimensional planning image is generated prior to positioning a patient associated with the patient anatomy on a movable couch of the radiation therapy system for acquiring the first X-ray image and the second X-ray image.

9. A radiation treatment system comprising:
- a gantry;
- an X-ray imaging system mounted on the gantry; and
- a processor configured to perform the steps of:
  - acquiring a first X-ray image of a region of patient anatomy while the region of patient anatomy is in a first location relative to an isocenter of the radiation therapy system, the gantry is in a first imaging position, and a center axis of an imaging beam passes through the isocenter of the radiation therapy system along a first imaging path;
  - acquiring a second X-ray image of the region of patient anatomy while the region of patient anatomy is in the first location, the gantry is in a second imaging position, and the center axis of the imaging beam passes through the isocenter of the radiation therapy system along a second imaging path, wherein an angle between the first imaging path and the second imaging path is a non-orthogonal angle; and
  - based on the first X-ray image, the second X-ray image, and a three-dimensional treatment planning image of the region, determining an offset between a planning location for the region and the first location of the region,
  - wherein determining the offset between the planned treatment position for the region and the first location of the region comprises iteratively applying a two-dimensional to three-dimensional matching algorithm to the first X-ray image, the second X-ray image, and the three-dimensional treatment planning image.

10. The radiation treatment system of claim 9, wherein the processor is further configured to perform the step of causing a movable couch of the radiation therapy system to reposition the region of patient anatomy based on the offset.

11. The radiation treatment system of claim 10, wherein the processor is further configured to perform the step of, in response to the movable couch repositioning the region, causing a treatment beam to be directed to the region.

12. The radiation treatment system of claim 10, wherein causing the movable couch to reposition the region comprises causing the movable couch to rotate or translate the region.

13. The radiation treatment system of claim 9, wherein the offset includes at least one of a linear displacement and a rotational displacement.

* * * * *